US006451352B1

(12) United States Patent
Yvin et al.

(10) Patent No.: US 6,451,352 B1
(45) Date of Patent: Sep. 17, 2002

(54) USE OF ISO-OSMOTIC SALINE SOLUTIONS, METHOD FOR PREPARING SAME AND MEDICINE BASED ON SAID SOLUTIONS

(75) Inventors: Jean-Claude Yvin, Saint Malo; Olivier Tabary, Reims; Jacky Jacquot, Reims; Edith Puchelle, Reims, all of (FR)

(73) Assignee: Laboratoires Goemar S.A., Saint Malo (FR)

(*) Notice: Subject to any disclaimer, the term of this patent is extended or adjusted under 35 U.S.C. 154(b) by 0 days.

(21) Appl. No.: 09/743,016

(22) PCT Filed: Jun. 29, 1999

(86) PCT No.: PCT/FR99/01565

§ 371 (c)(1),
(2), (4) Date: May 24, 2001

(87) PCT Pub. No.: WO00/00209

PCT Pub. Date: Jan. 6, 2000

(30) Foreign Application Priority Data

Jun. 29, 1998 (FR) .............................. 98 08250

(51) Int. Cl.[7] .................. A61K 33/00; A61K 33/06; A61K 33/14; A61K 35/02; A61K 9/72; A61K 35/08

(52) U.S. Cl. .................. 424/680; 424/600; 424/677; 424/678; 424/679; 424/681; 424/682; 424/722; 514/826; 514/849; 514/853; 514/886; 514/887; 514/888; 514/958

(58) Field of Search ................. 424/680, 600, 424/677–679, 681–682, 722; 514/826, 849, 853, 886, 887, 888, 958

(56) References Cited

FOREIGN PATENT DOCUMENTS

| CA | 1313142 | 1/1993 |
|---|---|---|
| FR | 2 688 133 | 9/1993 |
| FR | 2769503 | * 4/1999 |

OTHER PUBLICATIONS

Chemical Abstracts 131:9683, abstracting FR 2769503, 1999.*

The Encyclopedia of Chemistry, 3rd edition, Van Nostrand Reinhold co., New YOrk, pp. 746–748, 1973.*

Derwent Abstract, Accession No. 2000–160721, abstracting DE 69900690 E, 2002.*

Derwent Abstract, Accession No. 1976–91016X, abstracting FR 2299041 A, 1976.*

Holstrom, "Effect of Nasal Lavage on Nasal Symptoms and Physiology in Wood Industry Workers"; Rhinology, (Sep. 1997) XP002099566.

Seppey, "Comparative Randomised Clinical Study of Tolerability and Efficacy of Rhiomer Force 3 Versus A Reference Product In Post–Operative Care Of The Nasal Fossae After Endonasal Surgery", ORL: Journal of Oto–Rhino–Laryngology and its Related Specialties, (Mar.–Apr. 1996) 58 XP002099567.

Francois, "Non exteriorisated Acute Sinusitis in Children! Les Sinusites Aigues Nonexteriorisees de L'Enfant." Annales de Pediatrie, (1998) XP002099568.

* cited by examiner

*Primary Examiner*—John Pak
(74) *Attorney, Agent, or Firm*—Kilpatrick Stockton, LLP

(57) ABSTRACT

The invention concerns the use of iso-osmotic saline solutions in particular obtained from sea water, to obtain a medicine designed for a treatment preventing and limiting the release of chemical mediators responsible for causing inflammatory phenomena in the human respiratory tracts.

2 Claims, No Drawings

USE OF ISO-OSMOTIC SALINE SOLUTIONS, METHOD FOR PREPARING SAME AND MEDICINE BASED ON SAID SOLUTIONS

This application is a 371 of PCT/FR99/01565, filed on Jun. 29,1999

The invention relates to a medicine based on iso-osmotic, saline solutions. This medicine is intended for a treatment for preventing and limiting the release of the chemical mediators which are responsible for causing inflammatory phenomena in the respiratory tract, especially at the level of the nasal fossae and in the bronchia. In the case of certain diseases of the nasal fossae, defence reactions occur therein against aggressions caused by the often irritating products which are carried by the ambient air, the said defence reactions causing an accumulation of secretions which are mucous and mucous-purulent.

The said secretions cause obstructions of the nasal fossae.

It is already known to combat that type of obstructions by washing the nasal fossae with isotonic sea water.

A product with which excellent results have been obtained in that respect consists of isotonic sea water marketed under the trademark PHYSIOMER.

Furthermore, inflammations occur at the level of the mucous membranes in the respiratory tract; these inflammations may cause oedemea either at the level of the mucous membranes of the nasal fossae which in turn causes an obstruction phenomenon which makes breathing through nose impossible or possibly of the mucous membranes of the bronchia which cause pathologies of the bronchopneumopathy-type.

These inflammations are the results of an agression of the organism and more especially of the respiratory tract by the viruses and bacteria which are carried by the inhaled air and also by any other irritating and allergizing elements which are carried by the said air especially the pollen and any other products which are the source of the atmospheric pollution.

It is already known to combat that type of pathology by administration of agents which relieve congestion and which have a vaso-constrictive effect.

It is also known to use in that respect medicines which are based on corticosteroids.

The results obtained with the congestion relieving agents and with corticosteroids are satisfactory but the said agent present side-effects which are sometimes troublesome.

Consequently the object of this invention is especially to overcome the drawbacks of the prior art and to provide, for the treatment of the pathologies in consideration, a medicine which is free of side-effects.

And the applicant company—knowing that under the action of certain pro-inflammatory agents of bacterial origin, such as for example the lipopolysaccharide of P Aeruginosa or LPS, serotype 10 used at the concentration of 1 $\mu$g/ml, the human epithelial, glandular breathing cells release chemical mediators such as interleukine 8 which in turn cause the inflammatory phenomenae—has the merit of having found, after considerable search work, that the said object can be reached using a medicine obtained by the use of an iso-osmotic saline solution, especially iso-osmotic sea water, the said medicine being designed to a treatment adapted to prevent and to limit the liberation or freeing—under the influence of the pro-inflammatory agents comprising not only substances of bacterial origin but also viruses, bacteria and any other irritating and allergizing elements which are carried by the inhaled air—of the chemical mediators which are responsible for starting the inflammatory phenomenae of the mucous membranes of the human respiratory tract.

The iso-osmotic saline solution in question is characterized by:

a pH of from 7,8 to 8,3 a density of from 1,008 to 1,01 a content in dry matter of from 1 to 2% by weight an osmolarity of from 305 to 315 mOs/kg and a chemical constitution resulting, as far as its principal constituent elements are concerned, from the following table A:

TABLE A

| | |
|---|---|
| Sodium (Na) | from 2000 to 2600 mg/l |
| Potasium (K) | from 40 to 80 mg/l |
| Chloride (Cl) | from 5800 to 6000 mg/l |
| Calcium (Ca) | from 300 to 400 mg/l |
| Magnesium (Mg) | from 1200 to 1500 mg/l |

By way of consequence, the invention consists in the use of iso-osmotic saline solutions, especially obtained starting form sea water, for obtaining a medicine designed to a treatment limiting the release or freeing of the chemical mediators which are responsible for the starting of the inflammatory phenomenae of the mucous membranes of the human respiratory tract.

For the preparation of the above said iso-osmotic saline solutions, it is possible to proceed as follows:

The employed raw-material is a sea water taken for example at the depth of 5 to 10 meters in an area of strong movement of streams, the said raw-material being characterized by a salt content higher than 32 g/l.

Said water is analysed, decanted and then freed of its sodium using an electro dialysis technique in order to bring said water to isotonicity, i.e. to about 9 equivalent-grams of sodium chloride by liter, filtrated stored under sterile conditions especially in a vessel made of stainless steel.

It is then analysed again in order to check:

its sterility and its isotonicity (physiological).

It is then conditioned, preferably under controlled atmosphere in a room especially treated.

The research work which is on the basis of the invention comprises experiences showing that the iso-osmotique saline solution used according to the invention are less toxic than the well-known two reference products, i.e. the physiological serum and the PBS buffer while being better than these two products as far as their capacity to prevent and to limit the freeing of the chemical mediators is concerned, said mediators being responsible for the starting of the inflammatory phenomenae of the mucous membrane of the respiratory tract under the influence of the inflammatory agent.

The respective toxicities of the iso-osmotic saline solution used according to the invention, of the physiological serum and of the PBS buffer, have been determined using the comparative study of the viability in the presence of the said three products of the human respiratory cells, in other words, of the cells which occur in said respiratory mucous membranes.

In order to perform that study, human respiratory grandular cells taken off form human bronchia have been used.

The said respiratory epithelial cells were sowed at the same cellular density in culture plates comprising 12 holes.

The cells well cultivated during 48 hours in a culture medium denoted DMEMIF12 which had been complemented on the one hand with 2% of a nutriment consisting of the product marketed under the trademark ULTROSER G and on the other hand with a dose of antibiotics sufficient to avoid bacterial contamination; proceeding thus homogeneous and confluent mono-layer cultures were obtained, i.e. 310,000 cells per hole after 48 hours of culture.

At the moment at which confluence is reached, the cells are washed using a physiological solution (PBS/$Ca^{2+}$, pH 7.4) and put together with the iso-osmotic saline solution used according to the invention, with physiological serum, with PBS buffer and with a cellular culture medium playing the role of a reference and consisting of the culture medium known under the designation DMEM/F12.

After several incubations; which means cellular contact, i.e. 4 hours, 8 hours, 16 hours, and 24 hours, the cellular viability has been evaluated in the presence of the 4 above mentioned mediums.

The said cellular viability is defined by the percentage of viable cells at the end of each incubation period within the iso-osmotic saline solution used according to the invention, in the physiological serum and in the PBS buffer, with respect to the number of viable cells within the culture medium DMEM/F12.

The said cellular viability has been evaluated using the exclusion test called "Trypan bleu" in a 0.4% solution, the said test being followed by a numbering or enumeration using a Malassez cell.

According to the said test, the cells are removed from the culture support using trypsine; the living cells are then enumerated within a 0.4% aqueous solution of a Trypan bleu; in deed, Trypan bleu is a cellular dye which does not penetrate within the living cell; only not viable cells permit Trypan bleu to penetrate.

The number of living cells within the culture medium DMEM/F12 being by definition considered as being 100, it is possible to define the cellular viability within the other mediums by way of the percentage with respect to the culture medium.

The results of that study show that the iso-osmotic saline solutions use according to the invention authorise a better cellular viability during prolonged incubation periods, i.e. up to 24 hours of contact.

The recorded percentage of cellular viability, i.e. 58%, is higher than the one recorded with physiologic serum, i.e. 48% and a fortiori higher than the one recorded with the PBS buffer; that latter percentage is equal to zero, the viability of the cells within the buffer PBS being by way of consequence zero.

In Table B hereafter are collected the cellular viability percentages which are recorded in connection with the above experiences for incubation periods of 4, 8,16 and 24 hours.

TABLE B

| Medium | Cellular viability percentage Incubation periods | | | |
| --- | --- | --- | --- | --- |
| | 4 hours | 8 h | 16 h | 24 h |
| Iso-osmotic saline solution | 100 | 85 | 79 | 59 |
| Physiological serum | 100 | 81 | 72 | 49 |
| PBS buffer | 100 | 81 | 66 | 0 |
| Culture medium DMEM F/12 | 100 | 100 | 100 | 100 |

It clearly appears from the data recorded in Table B that the iso-osmotic saline solutions are distinctly less toxic than the physiologic serum and the PBS buffer.

In order to show the capability of the iso-osmotic saline solutions used according to the invention to prevent and to limit the liberation or freeing of the chemical mediators which are responsible of the starting of the inflammatory phenomenae of the mucous membrane of the human respiratory tract under the influence of the pro-inflammatory agents, the corresponding cellular cultures are incubated after stimulation by the pro-inflammatory agents, in the iso-osmotic saline solutions used according to the invention.

The experiences carried out by the applicant company were performed on glandular secretory cultures of the human bronchia hypo-mucous membrane.

In that connection, the said cells are cultured in a culture medium, for instance the RPMI1640 culture medium complemented with 2% of the ULTROSER G medium, then the culture medium is withdrawn after having reached at a 90% confluence and after the introduction of the pro-inflammatory agent consisting of the lipopolysaccharide of P. Aeruginosa or LPS, serotype 10 used at the concentration of 1$\mu$g/ml.

After washing of the thus treated cells, they are reincubated:

in the same RPMI 1640 culture medium alone which plays the role of the control medium, in physiological serum (0,9% NaCl solution as reference medium), in the iso-osmotic saline solution used according to the invention.

The production of the chemical mediator responsible of the starting of the inflammatory phenomenae, which consists of interleukine-8. by the glandular epithelial cells under the influence of the pro-inflammatory agents consisting of LPS, is estimated by the titration method ELISA (using the titration kit marketed under the trademark MEDGENIXDIAGNOSTIC, Belgium) after a contact period of one hour in the supernatants of the three above-identified mediums.

The results recorded with respect to the three above said mediums show that the production of interleukine-8 is of 121 pg/ml hour in the case of the RPMI 1640 medium, of 65 pg/ml hour in the case of the physiological serum, of 48 pg/ml hour in the case of the iso-osmotic saline solution according to the invention, which shows the superiority of the last one from the standpoint of view of its capability to prevent and to limit the liberation or freeing under the influence of the pro-inflammatory agents of the chemical mediators responsible for the starting of the inflammatory phenomenae of the mucous membranes of the respiratory tract.

These results have been confirmed by experiences carried out on the culture of a cellular line of respiratory surface epithelium (respiratory line 16-HBE).

In practice the iso-osmotic saline solution according to the invention is administered, i.e. given to the patient, in the form of aerosols or nebulisates or by instillation in the form of drops.

The present medicine is intended to a treatment limiting the liberation or release of the chemical mediators responsible of the starting of the inflammatory phenomenae of the mucous membranes of the human respiratory tract which occur in rhinopharingial and pulmonary diseases.

The iso-osmotic saline solution used according to the invention may be presented in the form of a nasal or a buccal aerosol for local action which acts on the mucous membranes of the human respiratory tract especially at the level of the nasal fossae and of the bronchia.

The usual posology may be of 2 puffs separated from one another by about 30 seconds and repeated 2 to 3 times per day by way of buccal inhalation according to the condition and the age of the patient.

In the case of the nasal inhalation, usually one or two puffs are administrated in each nostril, 3 to 4 times per day according to the condition and the age of the patient.

What is claimed is:

1. A method for limiting release of chemical mediators responsible for initiating inflammation of mucous membranes of a human respiratory tract, comprising administering to a patient an effective amount of sea water made iso-osmotic, the sea water being in the form of aerosols or nebulisates wherein the sea water comprises a pH of 7.8 to 8.3;

a density of from 1.008 to 1.01;

a dry matter content of from 1 to 2% by weight;

an osmolarity of from 305 to 315 mOs/kg; and a chemical composition comprising sodium in a concentration of from 2,000 to 2,600 mg/l, potassium in a concentration of from 40 to 80 mg/l, chloride in a concentration of from 5,800 to 6,000 mg/l, calcium in a concentration of from 300 to 400 mg/l, and magnesium in a concentration of from 1,200 to 1,500 mg/l.

2. The method according to claim 1, wherein the chemical mediators are released under the influence of pro-inflammatory agents comprising viruses, bacteria or irritating and allergizing elements carried inhaled air.

* * * * *